US008221678B2

(12) United States Patent
Hedman

(10) Patent No.: US 8,221,678 B2
(45) Date of Patent: Jul. 17, 2012

(54) SYSTEM AND PROCESS FOR REMOVING OR TREATING HARMFUL BIOLOGICAL AND ORGANIC SUBSTANCES WITHIN AN ENCLOSURE

(76) Inventor: David E. Hedman, Ojai, CA (US)

( * ) Notice: Subject to any disclaimer, the term of this patent is extended or adjusted under 35 U.S.C. 154(b) by 2428 days.

(21) Appl. No.: 10/371,826

(22) Filed: Feb. 20, 2003

(65) Prior Publication Data

US 2004/0028554 A1   Feb. 12, 2004

Related U.S. Application Data

(63) Continuation-in-part of application No. 10/313,901, filed on Dec. 5, 2002, now abandoned.

(60) Provisional application No. 60/358,222, filed on Feb. 20, 2002, provisional application No. 60/358,223, filed on Feb. 20, 2002.

(51) Int. Cl.
*A61L 2/00* (2006.01)
*A61L 9/00* (2006.01)
*A62B 7/08* (2006.01)
*B60H 3/00* (2006.01)
*A01M 1/20* (2006.01)
*F26B 19/00* (2006.01)
*F26B 7/00* (2006.01)

(52) U.S. Cl. .................. 422/1; 422/3; 422/28; 422/119; 422/125; 422/292; 422/305; 43/1; 43/124; 43/144; 34/380; 34/100; 34/201; 454/156; 454/159; 454/160

(58) Field of Classification Search ............ 422/1, 3–28, 422/119, 292, 305, 125; 43/124, 144, 1; 34/380, 100, 201; 454/156, 159, 160
See application file for complete search history.

(56) References Cited

U.S. PATENT DOCUMENTS

| 919,827 A | 4/1909 | Cochrane |
| 923,368 A | 6/1909 | Myser |
| 1,885,854 A | 11/1932 | Montellano |
| 1,943,613 A | 1/1934 | Lewis |

(Continued)

FOREIGN PATENT DOCUMENTS

CA   2205673   11/1998

(Continued)

OTHER PUBLICATIONS

Internet printout of "Preventing IAQ Problems at their source: Maintenance and Housekeeping", (Jan. 9, 2002).*

(Continued)

*Primary Examiner* — Jill Warden
*Assistant Examiner* — Monzer Chorbaji
(74) *Attorney, Agent, or Firm* — Kelly & Kelley, LLP

(57) ABSTRACT

A system and process is provided for removing or treating harmful biologic and organic substances within an enclosure, such as a container, building or vehicle. Air within the enclosure is heated to a predetermined temperature to kill organisms and cause harmful substances in the structure to migrate into the ambient air. Boric acid in combination with the heat may be used to kill mold and similar undesirable organisms. Temperature and pressure levels are monitored. The heated air carrying the harmful substances is passed through a filter to remove the harmful substances, and the heated air is recirculated to enhance efficiency. The system effectively kills insects, molds, viruses and bacteria and reduces the levels of allergens and volatile organic compounds in the structure.

30 Claims, 6 Drawing Sheets

U.S. PATENT DOCUMENTS

| | | | |
|---|---|---|---|
| 1,948,228 A | 2/1934 | Urban | |
| 2,040,110 A | 5/1936 | Tahvonen et al. | |
| 2,114,494 A | 4/1938 | Hummel et al. | |
| 2,171,315 A * | 8/1939 | Rennerfelt | 422/1 |
| 2,318,820 A | 5/1943 | Voigt et al. | |
| 2,386,676 A | 10/1945 | French | |
| 2,606,440 A | 8/1952 | Willey | |
| 3,041,684 A * | 7/1962 | Dawson et. al. | 422/292 |
| 3,107,974 A * | 10/1963 | Potapenko | 422/4 |
| 3,265,862 A | 8/1966 | Smith, Jr. et al. | |
| 3,420,439 A | 1/1969 | Meckler | |
| 3,505,989 A * | 4/1970 | Truhan | 600/21 |
| 3,748,803 A | 7/1973 | Widerby et al. | |
| 3,750,327 A | 8/1973 | Thybault | |
| 3,831,332 A | 8/1974 | Weese | |
| 3,846,072 A | 11/1974 | Patterson | |
| 3,964,268 A | 6/1976 | DiPeri | |
| 3,966,407 A * | 6/1976 | Zuckerberg et al. | 422/4 |
| 4,045,880 A | 9/1977 | Steffen | |
| 4,277,926 A | 7/1981 | Sherman et al. | |
| 4,597,192 A | 7/1986 | Sfondrini et al. | |
| 4,625,432 A | 12/1986 | Baltes | |
| 4,676,152 A | 6/1987 | Tsuji et al. | |
| 4,682,424 A | 7/1987 | Irving | |
| 4,817,329 A * | 4/1989 | Forbes | 43/124 |
| 4,823,520 A | 4/1989 | Ebeling et al. | |
| 4,864,942 A | 9/1989 | Fochtman et al. | |
| 4,902,315 A | 2/1990 | Spicer | |
| 4,918,857 A | 4/1990 | Wade et al. | |
| 4,953,320 A | 9/1990 | Nelson | |
| 4,955,146 A | 9/1990 | Bollinger | |
| 4,958,456 A * | 9/1990 | Chaudoin et al. | 43/124 |
| 4,961,283 A | 10/1990 | Forbes | |
| 4,989,363 A | 2/1991 | Doernemann | |
| 5,022,165 A | 6/1991 | Beswick | |
| 5,030,423 A * | 7/1991 | Obee et al. | 422/122 |
| 5,058,313 A | 10/1991 | Tallon | |
| 5,090,972 A | 2/1992 | Eller et al. | |
| 5,109,916 A | 5/1992 | Thompson | |
| 5,152,077 A | 10/1992 | Liang | |
| 5,155,924 A | 10/1992 | Smith | |
| 5,203,108 A | 4/1993 | Washburn, Jr. | |
| 5,219,226 A | 6/1993 | James | |
| 5,221,520 A * | 6/1993 | Cornwell | 422/122 |
| 5,226,244 A | 7/1993 | Carter et al. | |
| 5,293,700 A | 3/1994 | Ishii | |
| 5,348,704 A * | 9/1994 | Tanaka | 422/22 |
| 5,349,778 A | 9/1994 | Chu | |
| 5,369,892 A | 12/1994 | Dhaemers | |
| 5,378,086 A | 1/1995 | Campbell, Jr. et al. | |
| 5,387,403 A | 2/1995 | Ikeuchi et al. | |
| 5,442,876 A | 8/1995 | Pedersen | |
| 5,491,092 A | 2/1996 | Colvin | |
| 5,556,607 A | 9/1996 | Childers et al. | |
| 5,590,478 A | 1/1997 | Furness | |
| 5,590,830 A | 1/1997 | Kettler et al. | |
| 5,612,001 A | 3/1997 | Matschke | |
| 5,618,333 A * | 4/1997 | Buchholz et al. | 95/214 |
| 5,656,063 A * | 8/1997 | Hsu | 95/58 |
| 5,728,185 A * | 3/1998 | Buchholz et al. | 96/374 |
| 5,768,907 A | 6/1998 | Lee | |
| 5,806,238 A | 9/1998 | Brenner | |
| 5,874,050 A | 2/1999 | Matias | |
| 5,960,556 A | 10/1999 | Jansen | |
| 5,960,558 A | 10/1999 | Bourgault | |
| 5,979,472 A | 11/1999 | Lowery et al. | |
| 6,032,474 A | 3/2000 | Dale et al. | |
| 6,141,901 A | 11/2000 | Johnson et al. | |
| 6,162,393 A | 12/2000 | De Bruiju et al. | |
| 6,199,770 B1 | 3/2001 | King et al. | |
| 6,279,261 B1 * | 8/2001 | Binker et al. | 43/125 |
| 6,289,974 B1 | 9/2001 | De Gregoria | |
| 6,327,812 B1 | 12/2001 | Hedman et al. | |
| 6,383,449 B1 | 5/2002 | Pennekamp et al. | |
| 6,451,152 B1 | 9/2002 | Holmes et al. | |
| 6,494,934 B2 | 12/2002 | Fukushima | |
| 6,588,140 B1 * | 7/2003 | Johnson et al. | 43/124 |
| 6,612,067 B2 | 9/2003 | Topp | |
| 6,656,424 B1 * | 12/2003 | Deal | 422/3 |
| 6,878,177 B2 | 4/2005 | Lohr et al. | |
| 6,892,491 B2 | 5/2005 | Hedman | |
| 6,911,177 B2 | 6/2005 | Deal | |
| 6,962,619 B1 | 11/2005 | DeRosa et al. | |
| 7,690,148 B2 | 4/2010 | Hedman | |
| 2003/0100465 A1 | 5/2003 | Kilkenny et al. | |
| 2003/0230477 A1 | 12/2003 | Fink et al. | |
| 2004/0028554 A1 | 2/2004 | Hedman | |

FOREIGN PATENT DOCUMENTS

| | | |
|---|---|---|
| DE | 33 38 848 A1 | 5/1985 |
| DE | 3421719 A1 | 12/1985 |
| DE | 40 25 828 A1 | 2/1992 |
| DE | 42 05 459 A1 | 8/1993 |
| DE | 43 08 585 A1 | 9/1994 |
| EP | 676138 A1 | 10/1995 |
| EP | 0 676 138 A1 | 8/1997 |
| JP | 2187115 A | 7/1990 |
| JP | 2000116757 A | 4/2000 |
| WO | 9730802 A1 | 8/1997 |
| WO | 01/91858 A1 | 12/2001 |

OTHER PUBLICATIONS

Internet Printout of "Preventing IAQ Problems at their source: Maintainance and Housekeeping", (Jan. 9, 2002).*

"Volatile Organic Compounds and Building Bake-Out"—From the California Indoor Air Quality Program et al. Occupational Medicine: State of the Art Reviews—vol. 4, No. 4, Oct.-Dec. 1989, pp. 695-711.

G.A. Dean, "Heat for Mill Insects," Journal of Economic Entomology, 1913, pp. 40-55, vol. 6, Journal of Economic Entomology Publishing Co., Concord, New Hampshire.

Gary L. Servais, "Heat Sterilization Project", Journal, 1996, 60 pages, Brown & Williamson Tobacco Corporation, USA.

William Quarles, "Diatomaceous Earth for Pest Control", article, 1992, 16 pages, vol. XIV, No. 5/6, The IPM Practitioner, USA.

J. Coombs and K.E. Hall, "Dictionary of Biological Control and Integrated Pest Management", dictionary, 1998, 3 pages, CPL Scientific Publishing Services Limited, UK.

David Cain, "In Bed Bugs We Trust Inc. The Bed Bug University Summit", website, 2011, 2 pages, Pest Magazine, UK.

(Unknown), "Atlas Owner's Manual & Parts List", manual, 2008, 14 pages, EDIC, USA.

Michael D. Geyer, "Benefits of Dry Heat to Clean Structures of Biological Contamination and Improve Indoor Air Quality (IAQ)", article, 2002, 6 pages, SCS Engineers, USA.

Alan Forbess, "Turning Up the Heat: New Remediation Process for Water Damage Could Save Insurers 'Billions'", magazine, 2006, pp. 46 & 48, Canadian Underwriter, Canada.

Alan Forbess, "Heat Treatment Method Provides Water Damage/Mold Relief", journal, 2006, 3 pages, vol. 54, No. 5, Claims, USA.

Michael Geyer, "Mold Remediation with Heat", magazine, 2006, 3 pages, ICS Cleaning Specialist, USA.

(Unknown), "Project Watch: New Weapons in the War Against Mold", magazine, 2006, 4 pages, Multifamily Trends, USA.

Megan Headley, "Some Like It Hot: How Heat Has Become a Tool for Mold Remediation", magazine, 2006, pp. 20-22 & 24, Mold & Moisture Management Magazine, Key Communications, Inc., USA.

Mike Geyer, "Structural Pasteurization: Mold Remediation With Heat", magazine, 2006, 4 pages, Building Services Management, USA.

(Unknown), "New Heat Treatment Process Used for Mold Removal", website, 2006, pp. 1-3, www.tradelineinc.com, USA.

Joe McLean, "The Facts About Mold and Indoor Air Quality Using the New 'ThermaPure' Heat Treatment: Guide for Property Managers", manual, 2007, pp. 1-15, Alliance-Environmental Group, Inc. (Joe McLean), USA.

(Unknown), "Moisture Control, Mold, and the Science Within the Building Envelope", website, 2006, pp. 1-4, www.amazon.com, USA.

Anthony Manton, "Complex Solutions Made Simple", manual, 1988, pp. 1-49, Deep Sea Electronics PLC, UK.

(Unknonwn), "Thermal Pest Management Chamber for Heat Treatment (H.T.) Process", website, 2001, 5 pages, www.pestheat.com, Pest-Heat, USA.

(Unknown), "Thermal Remediation Pest Control Training Course", manual, 2010, pp. 1-24, Temp-Air, USA.

Michael R. Linford and William Currie, "Bedbugs Put the Bite on Hotel Business", article, 2006, 3 pages, Asian American Hotel Owners Association, USA.

Lisa Lupo, "Treating With Heat", article, 2008, 4 pages, Pest Management, USA.

(Unknown), "Benefits of Being a ThermaPureHeat Licensee", handbook, 2005, pp. 1-39, E-Therm, Inc., USA.

(Unknown), "ThermaPure, Inc. Receives New U.S. Patent for the Use of Heat Technology for Bed Bugs", 2010, article, 2 pages, ThermaPure, Inc., USA.

(Unknown), "Aggreko Heats Up the Food Industry", article, 1999, 1 page, Aggreko Inc., USA.

Alan K. Dowdy and Paul G. Fields, "Heat Combined with Diatomaceous Earth to Control the Confused Flour Beetle (Coleoptera: Tenebrionidae) in a Flour Mill", journal, 2002, pp. 11-22, Journal of Stored Products Research 38, Elsevier Science Ltd., USA Bhadriraju Subramanyam and David W. Hagstrum, "Inert Dusts", book, 2000, pp. 321-380, Chapter 12 of Alternatives to Pesticides in Stored-Product IPM, Kluwer Academic Publishers, USA.

(Unknown), "Diatomaceous Earth (DE)", website, 2000-2007, 6 pages, The Bluebird Box—Best of Bluebird Mailing Lists Classified, Audubon Society of Omaha, USA.

(Unknown), "Temp-Heat THP-1400, 2000, 3000, 4000 and 4500: Gas, Direct-Fired Temporary Heater Installation and Service Manual", manual, 2007, pp. 1-26, TempAir, Rupp Industries, Inc., USA.

(Unknown), "Temp-Heat THP-500HT: Gas, Direct-Fired Temporary Heater Installation and Service Manual", manual, 2002, pp. 1-17, TempAir, Rupp Industries, Inc., USA.

Albert C. Apt, "A Study of the Role of Vacuum Cleaning in the Control of Insects in Flour Mills", article, 1955, pp. 5-7, vol. 20, No. 8, Milling Production, USA.

George A. Dean, "Further Data On Heat As A Means of Controlling Mill Insects", journal, 1911, pp. 40-55, vol. 6, Journal of Economic Entomology, USA.

(Unknown), "Portable Industrial Unit Blower Air Heater Type DRA: Installation, Operation and Renewal Parts Identification", manual, 2002, pp. 1-6, Chromalox, Inc., USA.

(Unknown), "Temp-Heat ETHP-1500 and ETHP-1500 Electric Construction Heaters Installation and Service Manual", manual, 1998, pp. 1-15, TempAir, Rupp Industries, Inc., USA.

Jody Gangloff-Kaufmann and Jill Shultz, "Bed Bugs are Back! An IPM Answer", article, 2003, pp. 1-5, NYS Integrated Pest Management Program, USA.

(Unknown), "What Is Integrated Pest Management", article, 1997, pp. 3-8, Chapter 1, USEPA, Document #909-B-001 by the Bio-Integral Resource Center, USA.

C.L. Marlatt, "The Bedbug", bulletin, 1916, 17 pages, Farmer's Bulletin No. 754, U.S. Department of Agriculture, USA.

(Unknown), "Understanding the TPE Process", manual, 1999, 106 pages.

Mark Mire, "The History of Heat Sterilization for Pest Control", article, 1996, 107 pages, Aggreko, Inc., USA.

(Unknown), "Frequently Asked Questions About Bed Bugs, Their Bites, and How to Kill and Get Rid of Them", website, 2011, 6 pages, ThermaPure, Inc., USA.

(Unknown), "Guidelines on Assessment and Remediation of Stachybotrys Atra in Indoor Environments", based on panel discussion, 11 pages, 1993, New York, NY, USA.

Eckard Johanning, Philip R. Morey and Mark Goldberg, "Remedial Techniques and Medical Surveillance Program for the Handling of Toxigenic Stachybotrys Atra", article, 1993, vol. 4, pp. 311-316, Proceedings of Indoor Air, USA.

Pete Consigli, "Contaminated Crawl Spaces: the Good, the Bad, and the Ugly", symposium, 1996, 6 pages, ASCR 50th Convention, USA.

(Unknown), "Environmental Report #1", report, 1996, 9 pages, Safe Environments Home & Office Testing Services, USA.

James E. Holland and John Banta, "Developing Protocols and Technical Specifications: Chapter 1—Introduction", book, 1998, 10 pages, Restoration Hygiene Institute, USA.

James E. Holland, "Developing Protocols and Technical Specifications: Chapter 2—Project Planning", book, 1998, 8 pages, Restoration Hygiene Institute, USA.

James E. Holland, "Developing Protocols and Technical Specifications: Chapter 3—Containment Strategy", book, 1998, 32 pages, Restoration Hygiene Institute, USA.

James E. Holland, "Developing Protocols and Technical Specifications: Chapter 4—Safety Issues", book, 1998, 9 pages, Restoration Hygiene Institute, USA.

James E. Holland, "Developing Protocols and Technical Specifications: Chapter 5—Job Set Up Work Area Preparation", book, 1998, 28 pages, Restoration Hygiene Institute, USA.

James E. Holland, "Developing Protocols and Technical Specifications: Chapter 6—Work Procedures", book, 1998, 39 pages, Restoration Hygiene Institute, USA.

James E. Holland, "Developing Protocols and Technical Specifications: Chapter 7", book, 1998, 5 pages, Restoration Hygiene Institute, USA.

Joseph W. Lstiburek, "Mold, Moisture & Indoor Air Quality: A Guide for Designers, Builders, and Building Owners—Introduction", book, 1994, 14 pages, Building Science Corporation, USA.

Joseph W. Lstiburek, "Mold, Moisture & Indoor Air Quality: A Guide for Designers, Builders, and Building Owners—Chapter 1: People, Buildings, and the Environment", book, 1994, pp. 7-20, Building Science Corporation, USA.

Joseph W. Lstiburek, "Mold, Moisture & Indoor Air Quality: A Guide for Designers, Builders, and Building Owners —Chapter 2: HVAC Systems and Air Quality Problems", book, 1994, pp. 21-50, Building Science Corporation, USA.

Joseph W. Lstiburek, "Mold, Moisture & Indoor Air Quality: A Guide for Designers, Builders, and Building Owners—Chapter 3: Moisture Movement and Relative Humidity", book, 1994, pp. 51-62, Building Science Corporation, USA.

Joseph W. Lstiburek, "Mold, Moisture & Indoor Air Quality: A Guide for Designers, Builders, and Building Owners—Chapter 4: Microbial Contamination", book, 1994, pp. 63-68, Building Science Corporation, USA.

Joseph W. Lstiburek, "Mold, Moisture & Indoor Air Quality: A Guide for Designers, Builders, and Building Owners—Chapter 5: Cold Climate Mold, Mildew and Condensation", book, 1994, pp. 69-82, Building Science Corporation, USA.

Joseph W. Lstiburek, "Mold, Moisture & Indoor Air Quality: A Guide for Designers, Builders, and Building Owners—Chapter 6: Warm Climate Mold, Mildew and Condensation", book, 1994, pp. 83-112, Building Science Corporation, USA.

Joseph W. Lstiburek, "Mold, Moisture & Indoor Air Quality: A Guide for Designers, Builders, and Building Owners—Chapter 7: Vapor Diffusion Retarders, Air Retarders and Insulating Sheathings", book, 1994, pp. 113-128, Building Science Corporation, USA.

Joseph W. Lstiburek, "Mold, Moisture & Indoor Air Quality: A Guide for Designers, Buliders, and Building Owners—Chapter 8: Case Studies", book, 1994, pp. 129-244, Building Science Corporation, USA.

Michael A. Berry, "Protecting the Built Environment: Cleaning for Health", book, 1993, 84 pages, Tricomm 21st Press, USA.

(Unknown), "ASHRAE Handbook: 1983 Equipment Volume", handbook, 1983, 78 pages, American Society of Heating, Refrigerating and Air-Conditioning Engineers, Inc., USA.

(Unknown), "1996 ASHRAE Handbook: Heating, Ventilating, and Air-Conditioning—Systems and Equipment", handbook, 1996, 194 pages, American Society of Heating, Refrigerating and Air-Conditioning Engineers, Inc., USA.

(Unknown), "ASHRAE Handbook: 1982 Applications", handbook, 1982, 84 pages, American Society of Heating, Refrigerating and Air-Conditioning Engineers, Inc., USA.

(Unknown), "ASHRAE Handbook: 1984 Systems", handbook, 1984, 104 pages, American Society of Heating, Refrigerating and Air-Conditioning Engineers, Inc., USA.

(Unknown), "1995 ASHRAE Handbook: Heating, Ventilating, and Air-Conditioning Applications", handbook, 1995, 232 pages, American Society of Heating, Refrigerating and Air-Conditioning Engineers, Inc., USA.
(Unknown), "The Dehumidification Handbook", handbook, 1982, 67 pages, The Cargocaire Engineering Corporation, USA.
(Unknown), "The Dehumidification Handbook", handbook, 1990, 2nd Ed., 153 pages, Munters Cargocaire, USA.
(Unknown), "Design Considerations for Toxic Chemical and Explosives Facilities", symposium, 1987, 33 pages, American Chemical Society, USA.
Seymour S. Block, "Disinfection, Sterilization, and Preservation", 3rd Ed, book, 1983, 160 pages, Lea & Febiger, Philadelphia, PA, USA.
W.A. Murray, A.J. Streifel, T.J. O'Dea, F.S. Rhame, "Ventilation for Protection of Immune Compromised Patients", journal, 1988, pp. 1185-1191, vol. 94, USA.
John R. Girman, Leon E. Alevantis, George C. Kulasingam, Myrto X. Petreas, and Lurance M. Webber, "The Bake-Out of an Office Building: A Case Study", study, 1989, Environmental International, vol. 15, pp. 449-453, Pergamon Press, USA.
Ernie Storrer, "Mold & Trapped Moisture", article, 1997, 2 pages, Cleaning and Restoration, Injectidry Systems, Inc., USA.
(Unknown), "The 'Mobile Hands-On' Water Damage Restoration Technician School: Interactive Student Manual", manual, 2000, 292 pages, Aspire Educational Institute & Conference Centre, Costa Group, Inc., USA.
Clifford B. Ziotnik, "Microban Systems, Inc. Water Restoration Technology Manual", manual, 2002, 96 pages, Microban Systems, Inc., USA.
Michael A. Pinto and David Janke, "Fungal Contamination: A Comprehensive Guide for Remediation", handbook, 2001, 329 pages, Wonder Makers Environmental, Inc., USA.
Bill Lundquist et al., "Assessment, Cleaning, and Restoration of HVAC Systems", manual, 2006, 52 pages, National Air Duct Cleaners Association (NADCA), USA.
(Unknown), "A Brief Guide to Mold in the Workplace", bulletin, 2010, 51 pages, Office of Science and Technology Assessment, USA.
(Unknown), "Mold Remediation in Schools and Commercial Buildings", manual, 2001, 70 pages, U.S. Environmental Protection Agency, USA.
Joseph A. Hughes, "Indoor Environmental Contractor Program: Microbial Remediation Supervisor", manual, 2003, 231 pp., IAQ Training Institute LLC, USA.
William Quarles, "Thermal Pest Eradication in Structures", newsletter, 2006, 8 pages, vol. 28, Issue 5/6, The IPM Practitioner, USA.
George A. Dean, "Further Data on Heat as a Means of Controlling Mill Insects", journal, 1913, pp. 40-55, vol. 6, Journal of Economic Entomology Publishing Co., USA.
(Unknown), "Standard and Reference Guide for Professional Water Damage Restoration (IICRC S500)", manual, 1994, 360 pages, Institute of Inspection, Cleaning and Restoration (IICRC), USA.
(Unknown), "Standard and Reference Guide for Professional Mold Remediation (IICRC S520)", manual, 2003, 239 pages, Institute of Inspection, Cleaning and Restoration (IICRC), USA.
(Unknown), "Electric Thermal Energy System Operator's Manual (120 Volt)", manual, 2010, 44 pages, Bridgepoint Systems, USA.
(Unknown), "Electric Thermal Energy System Operator's Manual (240 Volt)", manual, 2009, pp. 1-4, 7-39, Bridgepoint Systems, USA.
George A. Dean, "Heat as a Means of Controlling Mill Insects", Journal, 1911, pp. 142-161, vol. 4, Journal of Economic Entomology Publishing Co., USA.
W.C. O'Kane and W.A. Osgood, "Studies in Termite Control", Bulletin, 1922, pp. 1-20, Bulletin No. 204, New Hampshire College of Agriculture and the Mechanic Arts, USA.
U.S. Department of Agriculture, "Insect Control in Flour Mills", Handbook, 1958, pp. 23-25, Agriculture Handbook No. 133, U.S. Government Printing Office, USA.
(Unknown), "The Way Things Work", 1967, pp. 248-249, 262-265, Simon & Schuster, USA.
R. Elsworth, "Treatment of Process Air for Deep Culture", Book, 1969, pp. 129-135, vol. 1, Chapter 4, Academic Press Inc., London and New York.
David A. Sterling, C. Clark, and S. Bjornson, "The Effect of Air Control Systems on the Indoor Distributions of Viable Particles", Study, 1982, pp. 409-414, Environment International, vol. 8, Pergamon Press, Ltd., USA.
Kenneth O. Sheppard, "Heat Sterilization (Superheating) as a Control for Stored-Grain Pests in a Food Plant", Book, 1984, pp. 193-200, American Association of Cereal Chemists, USA.
Charles Forbes and Walter Ebeling, "Use of Heat for Elimination of Structural Pests", Newsletter, 1987, pp. 1-5, vol. 9, Issue 8, IPM Practitioner, USA.
Walter Ebeling, Charles F. Forbes and Sandra Ebeling, "Heat Treatment for Powderpost Beetles", Newsletter, 1989, pp. 1-4, vol. 11, Issue 9, IPM Practitioner, USA.
Stewart Brand and Richard Kadrey, "The Chronicle Whole Earth Catalog Briefing: Safe Homes/The Toxic-Free House", Article, 1991, pp. 1-3, San Francisco Chronicle, USA.
David W. Bearg, "Indoor Air Quality and HVAC Systems", Book, 1993, pp. 1-209, CRC Press, USA.
Paul Stamets, "Growing Gourmet and Medicinal Mushrooms", Book, 1993, pp. 171-173, Ten Speed Press, USA.
Walter Ebeling, "The Thermal Pest Eradication System for Structural Pest Control", Newsletter, 1994, pp. 1-7, vol. 16, Issue 2, The IPM Practitioner, USA.
M. Nicholson and W. Von Rotberg, "Controlled Environment Heat Treatment as a Safe and Efficient Method of Pest Control", Symposium, 1996, pp. 263-265, Thermo Lignum UK Ltd., UK.
Lisa G. Neven and Elizabeth J. Mitcham, "CATTS (Controlled Atmosphere/Temperature Treatment System): A Novel Tool for the Development of Quarantine Treatments", Research, 1996, pp. 56-59, American Entomologist, USA.
Jerry Heaps, "Heat for Stored Product Insects", Newsletter, 1996, pp. 18-19, vol. 18, Issues 5-6, The IPM Practitioner, USA.
David Pinniger, "Insect Control With the Thermo Lignum Treatment", Newsletter, 1996, No. 59, Conservation News, UK.
(Unknown), "Dri-Eaz Owner's Manual for Dri-X AirChanger", Manual, 1997, pp. 1-14, Dri-Eaz Products, Inc., USA.
John Gladstone and W. David Bevirt, "HVAC Testing, Adjusting, and Balancing Manual", Manual, 1997, pp. 94-101, 167-169, 172-175, 287-301, Third Edition, McGraw-Hill, USA.
U.S. Army Center for Health Promotion and Preventive Medicine, "Procedures for Thermal Control of Cockroaches in Army Food Service Facilities", Manual, 1997, pp. 1-1 thru H-1, USACHPPM Technical Guide No. 208, U.S. Government, USA.
Walter Ebeling, "Expanded Use of Thermal Pest Eradication (TPE)", Newsletter, 1997, pp. 1-8, vol. 19, Issue 8, The IPM Practitioner, USA.
R. Joseph Woodrow and J. Kenneth Grace, "Cooking Termites in the Aloha State", Article, 1997, pp. 1-3, Advanstar Communications Inc., USA.
Michael K. Rust and Donald A. Reierson, "Temperature Sensitivity in Insects and Application in Integrated Pest Management", Book, 1998, pp. 179-200, Westview Press, USA.
Brian C. Zeichner, Alfred L. Hoch and Donald F. Wood, Jr., "Heat and IPM for Cockroach Control", Newsletter, 1998, pp. 1-6, vol. 20, Issue 2, The IPM Practitioner, USA.
William Quarles, "Pest Control Operators and Heat Treatment", Newsletter, 1994, p. 8, vol. 16, The IPM Practitioner, USA.

* cited by examiner

SYSTEM AND PROCESS FOR REMOVING OR TREATING HARMFUL BIOLOGICAL AND ORGANIC SUBSTANCES WITHIN AN ENCLOSURE

RELATED APPLICATIONS

This is a continuation-in-part of U.S. patent application Ser. No. 10/313,901, filed Dec. 5, 2002 now abandoned. Priority is further claimed from U.S. Provisional Application Serial Nos. 60/358,222, and 60/358,223, both filed Feb. 20, 2002.

BACKGROUND OF THE INVENTION

The present invention relates to methods of sanitizing buildings, passenger occupiable vehicles, and other enclosed or enclosable spaces. More particularly, the present invention relates to a system and method for killing and removing insects, dust mites and their allergens, bacteria, viruses, fungi, molds, and volatile organic compounds from such enclosures.

A large number of methods have been developed for killing insects, such as termites, in buildings. The most widely used method is tenting the building, then filling the building with a toxic gas for a period of time sufficient to kill termites or other selected insects. This method is effective for killing termites and other insects. However, this method generally requires 12 hours to be effective, requiring building occupants to move out and businesses to be closed for approximately a three day period to insure proper venting of toxic material and/or gas. Tenting the building with heavy tarpaulins requires workers to walk and arrange the tarpaulins on the roof, often damaging the roof system. Food and medications must be placed in sealed containers or removed. Generally the entire building must be treated, even if the infestation is localized.

Techniques of varying effectiveness have been developed using heated air or very cold air to kill termites and other organisms. Typical of these are the methods disclosed by Charles Forbes in U.S. Pat. No. 4,817,329, and Hedman et al. in U.S. Pat. No. 6,327,812 in which wood destroying insects, e.g., termites, are killed by applying a heated gas, such as heated air, to wooden surfaces or the like until the core of wooden structures is heated to a temperature typically about 120° F. to 135° F. Temperatures for killing other insects are said to be surprisingly close to this range. This method has been found to be very effective for killing termites. Another alternative to the toxic gas method is disclosed by James J. Chaudoin, et al. in U.S. Pat. No. 4,958,456, in which insects, e.g., roaches, fleas and beetles, are killed by a treatment of building spaces with boric acid and heat. However, the methods disclosed in the Forbes and Hedman et al. patents are quite complex in the preparation of the building. An enclosing tent structure must be formed around the structure to be decontaminated. Tenting the building with heavy tarpaulins requires workers to walk and arrange the tarpaulins on the roof, often damaging the roof system.

Also, these methods, using the described temperatures, is not effective for other organisms, such as fungi, and molds such as, but not limited to, *aspergillus oryzae, aspergillus terreus, aspergillus versicolor, cladosporium hergbarum, stachybotrys chartarum, penicillium aurantiogriseum, pencillium chrsogenum, pencillium gladrum* and *fusarium oxysporum*. Further, many such fungi, molds and the like are a serious health hazard even when dead. Many people are allergic to the dust-like remains and residue, i.e., allergens, of these organisms that can also cause serious health problems. This is a particular problem to persons suffering from asthma, bronchitis, pneumoconious and other respiratory ailments, and is a common contributing factor to sick building syndrome (SBS).

It is also well-known that the heated air causes certain molds, fungi, etc. to sporulate, thus releasing spores into the structure and thus dispersing the harmful biological agents and possibly contaminating the structure to a greater degree than originally presented. The use of positive pressure within the structure, as described in Forbes and Hedman et al., further increase the likelihood that the biological contaminants will be dispersed throughout the structure. Forbes and Hedman et al. also disclose that the heated air can be vented from open windows and the like. However, when treating a contaminated building having harmful viruses, toxic molds, etc., it is not desirable to release such contagions into the air.

Volatile organic compounds (VOCs) have also been implicated as a possible cause of SBS. VOCs can originate from a variety of sources. Commercial examples include by-products of printing shop operations, office machine repairs, blueprint production, photographic processing and food service operations. In residences, such VOCs can include hobbyist products, cosmetics, perfumes, personal hygiene products, aerosol sprays, tobacco smoke, pet urine and even small emissions from the bodies of the occupants. Off gassing of VOCs is often a common by-product of various building/construction materials, for example paints, adhesives, plastics, carpeting, etc.

Such VOCs are implicated with SBS for mostly two reasons. First, the health effects from exposure to VOCs are consistent with SBS, ranging from irritant effects such as unpleasant odors and mucous membrane irritation, through general systemic effects such as fatigue, nausea, and difficulty concentrating. In addition, they may be of importance because some of them have been shown to have carcinogenic or adverse reproductive effects. Second, indoor concentrations of VOCs, particularly in new buildings, are often greatly elevated with respect to outdoor VOC concentrations. In fact, indoor VOC concentrations have typically been found to be two to ten times higher then outdoor concentrations, and indoor concentrations as much as 100 times higher than outdoor concentrations have been reported in new buildings.

Passenger occupiable vehicles, such as trains, buses, airplanes, etc. also include building/construction materials which are known to off gas VOC's. Also, the fuel, oil, and grease fumes and odors can infiltrate the passenger compartments of such vehicles and build-up within the seats, carpets, etc. over time. Due to the great number of people regularly traveling in such vehicles, there is an increased chance of coming into contact with contagious bacterium or viruses that can cause illness. Other organisms, such as fungi, and toxic molds can also be potentially found in such vehicles. As the company owning such vehicles necessarily must keep the vehicles running nearly constantly in order to realize the expected profit, such vehicles are rarely cleaned thoroughly. Even if the surfaces are superficially vacuumed and wiped down, there still remain live and dead organisms such as lice, mites, fungi, toxic molds, bacterium, viruses, VOCs, oxidized odors, and potentially insects which may have infested the vehicle, particularly those where food is prepared or served.

There are also instances when personal articles and small pieces of furniture need to be treated. For example, bedding and mattresses over time can accumulate a large amount of allergens, in the form of dust mites and their allergens, etc. Furniture may also experience water damage, causing fungi and toxic molds to grow thereon. These articles may also need to be treated for contagious bacterium or viruses that can cause illnesses.

Accordingly, there is a need for a system and method for killing and removing biological organisms and reducing odors and volatile organic compounds in enclosures such as commercial and residential buildings, boats, vehicles and portable containers. Such a method should be non-toxic and performed in a relatively short amount of time. Such a method should also effectively kill and remove a large proportion of the dead organisms and substantially reduce volatile organic compounds. The present invention fulfills these needs and provides other related advantages.

SUMMARY OF THE INVENTION

The present invention resides in a system which removes or treats harmful organic substances within an enclosure, such as a building, vehicle, container, erectable enclosure or other enclosed structure. Larger structures are typically prepared by positioning a plurality of probes, such as temperature probes and pressure measuring devices, at predetermined locations within the structure. Heat-sensitive articles within the structure are protected. This can be done by covering the articles with an insulated mat. Also, fans can be positioned adjacent to the heat sensitive articles for directing the flow of heated air away from the articles during the decontamination process. The contaminated area of the structure may also be physically cleaned in preparation of decontamination. This can be done by wiping, scraping, vacuuming, etc. the mold or other harmful organisms which are accessible and can be easily cleaned and removed. In one embodiment, borate, such as boric acid or the like, is applied to selected areas of the enclosure to kill molds and fungi.

The ambient air within the structure is then heated to a predetermined temperature of between 110° F. and 400° F., typically by directing and distributing heated air into the enclosed structure. This causes the harmful substances in the structure to be destroyed, neutralized, oxidized, or migrate into the ambient air. A biocide or even moisture, may be added to the heated air to enhance the treatment. Preferably, the air within the structure is aggressively moved using blowers, fans, or the like to aerosolize the biological and organic substances to facilitate their removal. The temperature of the structure is monitored until the predetermined temperature is achieved. The pressure levels within the structure are also monitored to verify adequate pressure, which is typically a negative pressure to facilitate removal of the harmful substances.

The heated air carrying the harmful substances is then removed from the structure through a filter. The filter preferably comprises a high efficiency particulate arrestance filter. Preferably, the filtered and heated air is re-circulated into the enclosure. In a particularly preferred embodiment, after a predetermined time period of directing heated air within the structure, the non-heated ambient air is directed into the structure, while continuing to remove the air through the filter. In certain instances, the contaminated portion of the structure is then physically cleaned after these steps have been performed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings for purposes of illustration, the present invention is related to a system and method for removing harmful organic substances, such as VOCs, dust mites and their allergens, bacteria, termites and other insects, from an enclosure.

Figure 1:
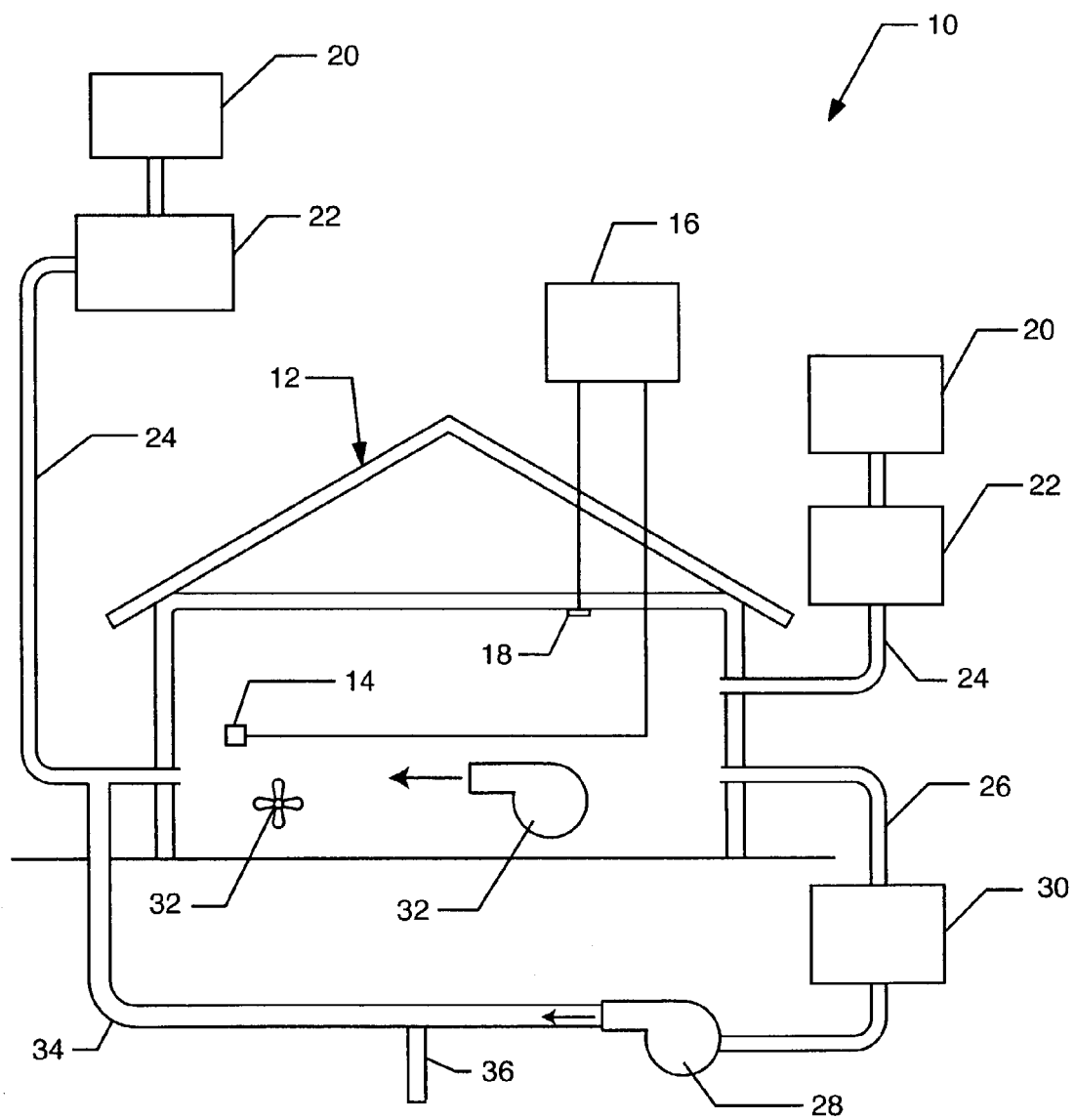
FIG. 1 is a schematic diagram showing components of the system of the present invention installed for treatment of a building.
Figure 2:
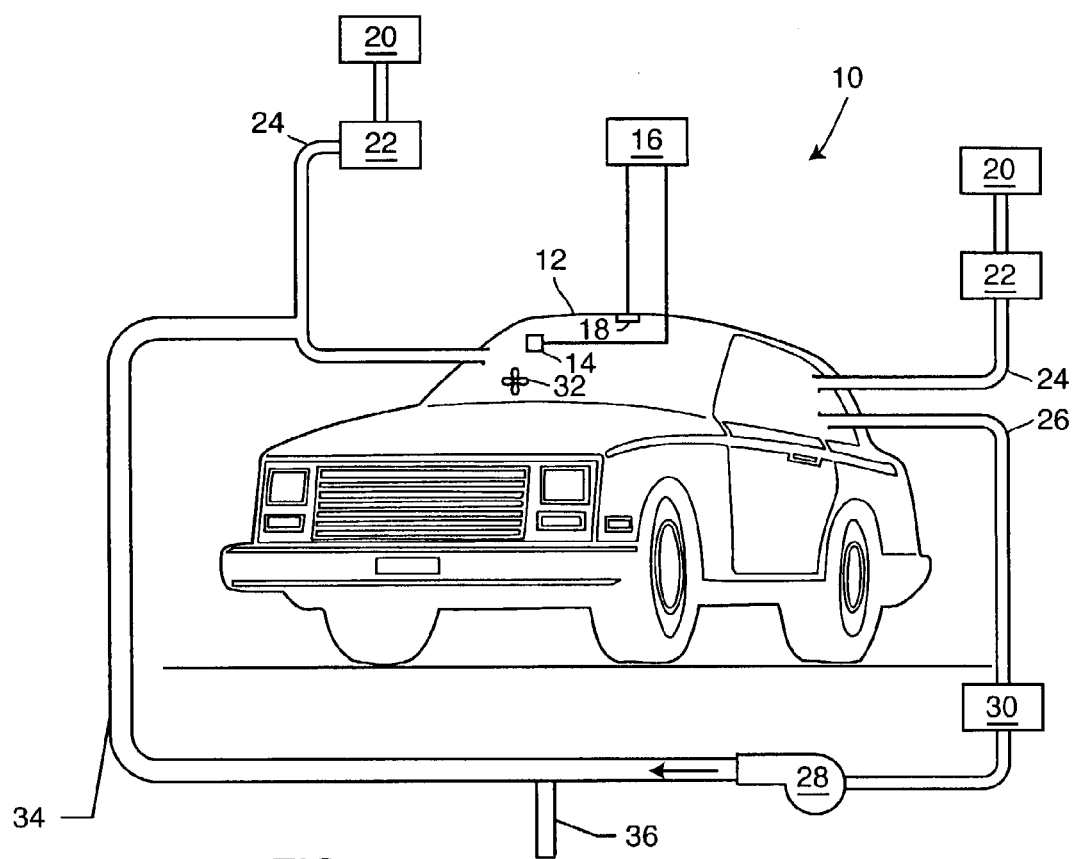
FIG. 2 is a schematic diagram showing an automobile treated in accordance with the present invention.
Figure 3:
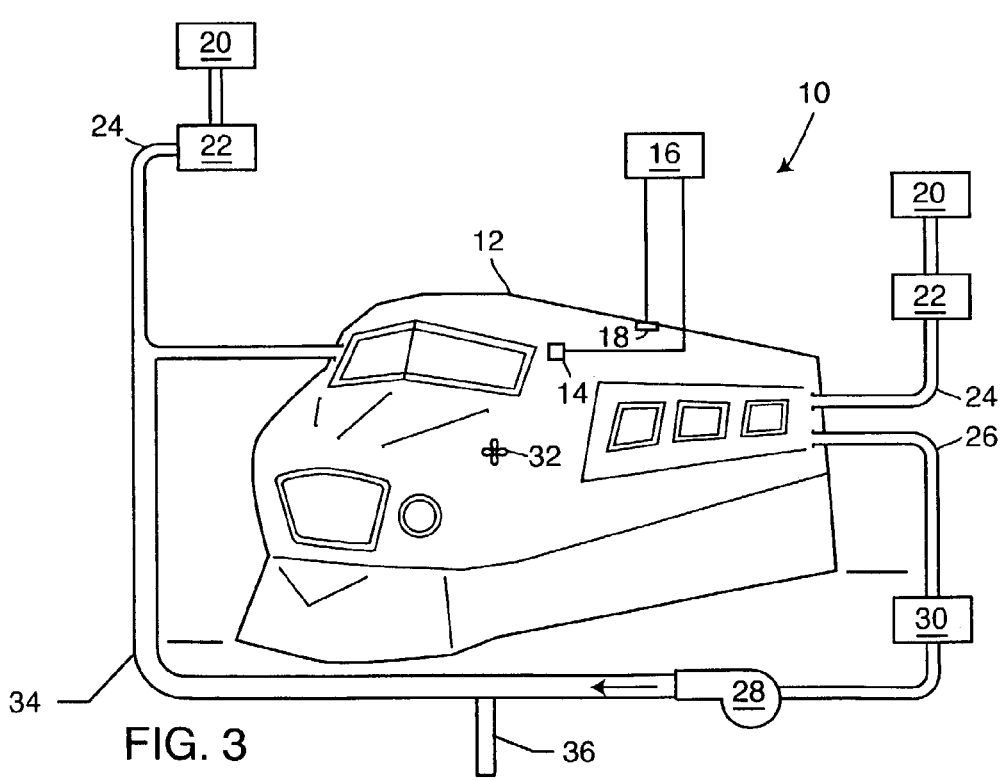
FIG. 3 is a schematic diagram illustrating a train being treated in accordance with the present invention.
Figure 4:
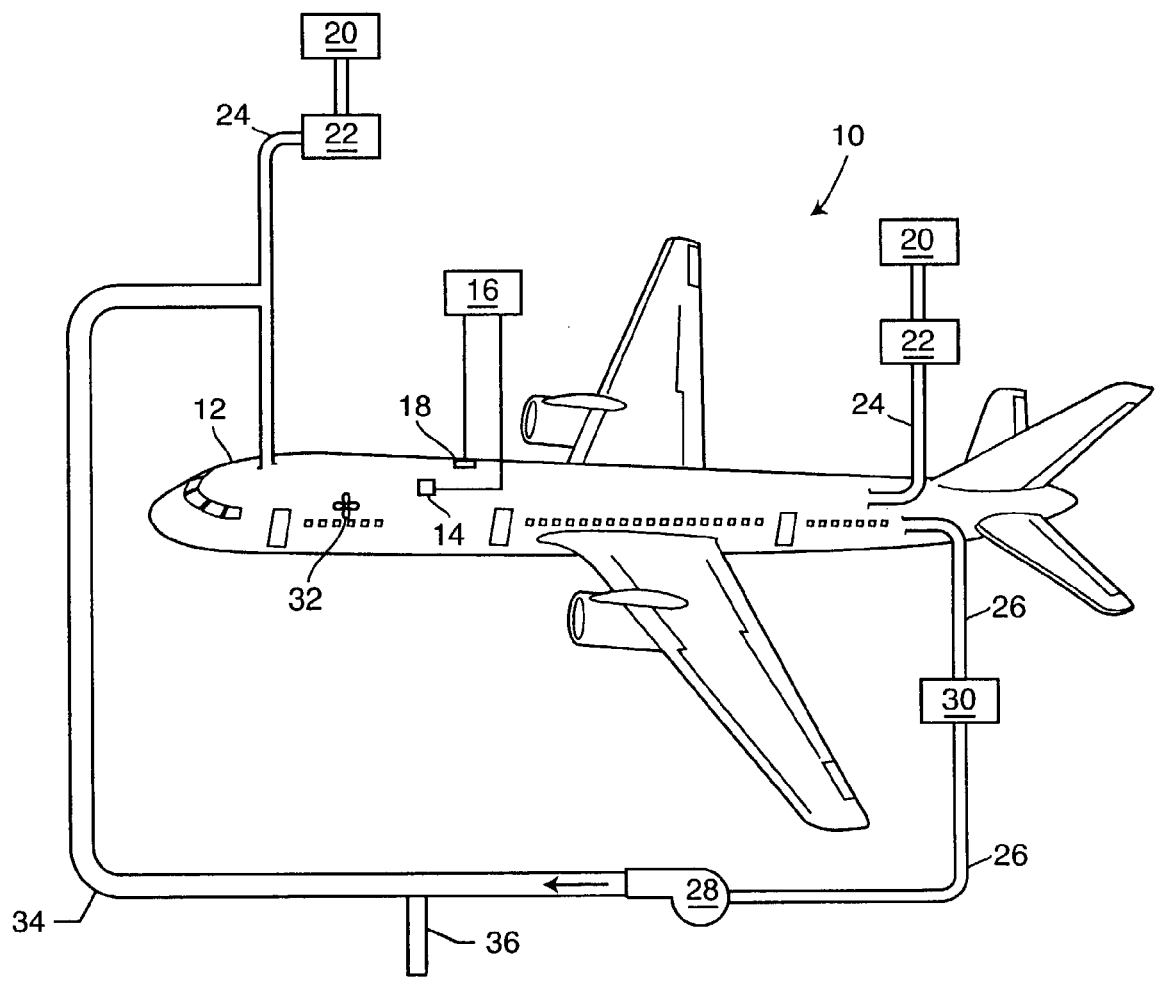
FIG. 4 is a schematic diagram of an airplane being treated in accordance with the present invention.
Figure 5:
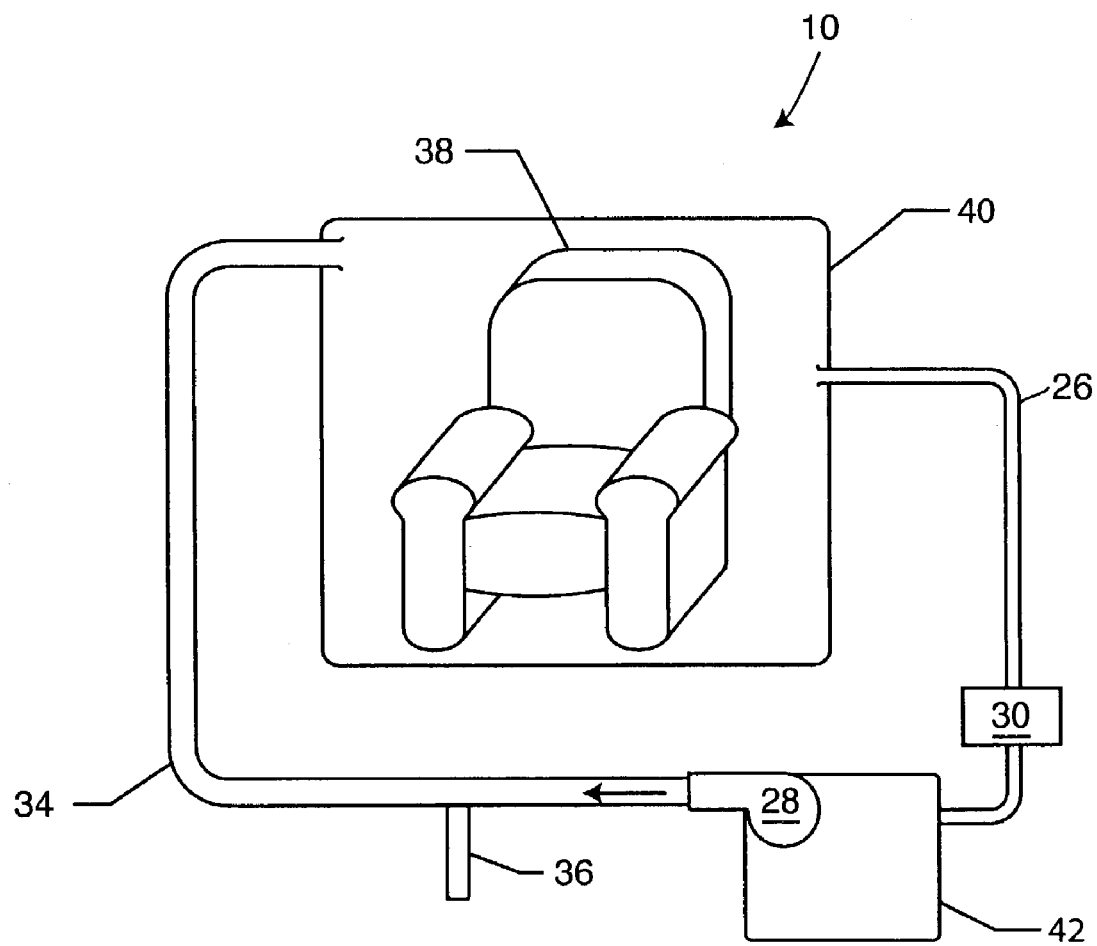
FIG. 5 is a schematic diagram illustrating a portable decontamination system used in accordance with the present invention to treat smaller objects.

Referring to FIGS. 1-4, there is seen a schematic diagram showing the components of the system of the present invention, referred to generally by the reference number 10, in use treating an enclosed structure 12. The enclosed structure 12 is typically a commercial or residential building, but can also be a vehicle, such as an airplane, bus, boat, automobile, etc., as shown in FIGS. 2-4.

A plurality of temperature sensors 14 are positioned at predetermined locations within the structure to monitor the temperature of the structure 12. Typically, these sensors 14 have thin, elongated tips that can be adhered to or pushed into materials to be heated or into suitably sized holes drilled into such materials so as to measure the surface and/or internal temperature. The sensors 14 may be wired to a console 16 which displays and records the temperature at each sensor 16 in real time. Alternatively, the sensors 14 may be wireless and transmit a signal to the console 16. Typical sensors 14, as for way of example and not by way of limiting, include thermal couples, thermistors, or the like connected to a computer and/or a strip chart recorder console 16.

A pressure measuring device, such as a manometer 18, is positioned within the structure 12 so as to measure the internal pressure of the structure 12 during operation of the invention. As will be more fully described herein, in some instances, positive air pressure is desirable. However, in most instances, a negative pressure is established and maintained throughout the operation of the method of the present invention in order to prevent the dispersal of harmful biological and organic contaminants throughout the structure 12. The manometer 18 can be linked to the console 16 to provide the pressure information from without the structure 12.

One or more heaters 20 heat air to a predetermined temperature lethal to the organisms to be destroyed. For a more complete disinfection, the air temperature is preferably raised to at least about 155° F., with optimum results generally achieved with temperatures in the range of about 110° F. to 400° F., or higher. A biocide, having desirable characteristics enhanced by heat, may be introduced with the heated air. Moisture may also be introduced with the heated air.

Any suitable heater 20 may be used. A gas burning heating device 20, such as a conventional propane heater, is preferred as being particularly efficient in heating air. Any other heating arrangement, such as electrical devices, solar heaters, and light emitting devices, may be used if desired.

The air can be heated directly within the structure 12, however, the heated air is usually injected into the structure 12. Heated air (and biocide, if used) from the one or more heaters 20 is directed through blower 22 (which may, if desired, be a component of the heater 20) which injects the hot air into the enclosed structure 12 through at least one inlet duct 24. Generally, a plurality of inlet ducts 24 will be used to achieve the optimum distribution of hot air throughout the enclosed structure 12. The inlet ducts 24 preferably include variable flow dampers and may be moved while the system is in operation to achieve uniform temperatures in all areas of the structure being treated, as sensed by sensors 14 and observed at console 16.

At least one outlet duct 26 is provided to allow the air to be removed from the structure 12. A blower or vacuum 28 is connected to the outlet duct 26 in order to remove air from the interior of the structure 12. Vacuum 28 may be used to create a negative pressure within the structure 12. Typically, this negative pressure is created before the heated air is introduced into the structure 12. The removed air is filtered, typically utilizing a high particulate arrestance filter, ULPA filter, or the like coupled with the vacuum/blower 28. Other filters such as charcoal filters or UV filters may be employed as well. The filter or air scrubber 30 removes the remains of the organisms and VOCs from the air to prevent them from reaching the environment or being re-introduced into the structure 12.

Preferably, additional blowers 32 or fans are positioned within the structure 12 to aggressively move the air within the structure to further enhance the removal of harmful biological and organic substances by aerosolizing the biological and organic substances and aid in heat distribution. Additionally, fans 32 may be positioned strategically within the structure 12 to selectively move the air away from predetermined heat-sensitive articles or areas of the structure in which such an elevated temperature is not desired. Typically, however, such heat-sensitive articles are removed from the structure or covered with insulation mats or the like.

In a particularly preferred embodiment, the filtered air is re-directed through duct 34 into the structure 12, such as by linking duct 34 with inlet 24. Such re-circulation of heated air enhances the energy and thermal efficiency of the process and decreases the overall treatment time. Additionally, it has been found that merely venting the air into the environment causes heat dilution and stratification to occur within the structure 12. Re-circulating the filtered and heated air reduces the heat dilution and stratification, and has been found to increase treatment air circulation within the containment area of the structure 12. The re-circulated air may be blended with the heat processed air as it exits the heater barrel, re-heated by the heater 20 or simply re-introduced by way of ducting into the structure 12.

Although the above description has been directed to rather large structures, such as residential or commercial buildings and passenger occupiable vehicles and the like, the present invention can also be applied to treatment of much smaller areas or objects. For example, a single room of a building may be treated by sealing the windows, doors, and other passageways of that particular room or area and treating such area, as described above. There are also instances where small personal articles, such as clothing or bedding, or even furniture is required to be treated, but not the structure itself.

As illustrated in FIG. 6, the present invention can be adapted for treatment of such articles 38. A common instance of treatment is the destruction or removal of allergens such as dust mite feces and the like from bedding and mattresses. Dust mite feces are known to cause mild and even severe allergic reactions in some individuals. These individuals may have headaches, runny noses, persistent coughs, etc. which is not caused by an infection, but rather allergic reaction to the allergens. The personal articles 38, in the form of bedding or the like, is placed within a portable structure 40. Such portable structure 40 may comprise a rigid and portable structure of sufficient size to treat the articles. For example, the back of a van may be converted into a treatment containment area. Alternatively, an inflatable bag, typically comprised of appropriate thermal material, is used. The personal articles 38 would be placed within such a thermal envelope or bag 40 and heated air directed into the inlet thereof. Pressure and temperature could be monitored and controlled using a device 42 attached to the portable structure 40. Preferably, the heated air which is removed is passed through a filter 30 and re-circulated, as described above. If toxic molds or fungi are of a concern, the air temperature may be reduced over time to prevent sporulation and the like.

Figure 6A:
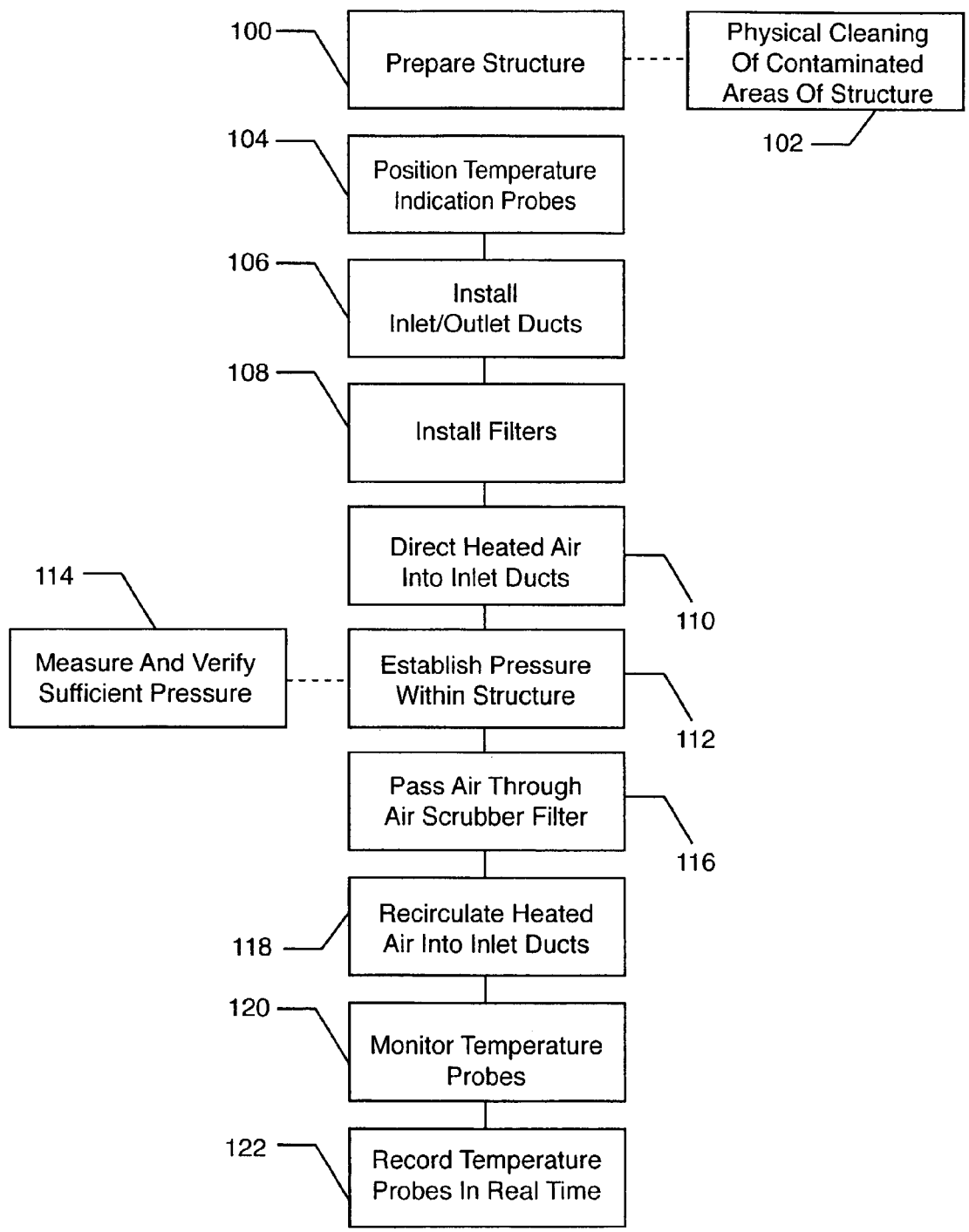
FIGS. 6A and 6B are flow diagrams illustrating the method used in accordance with the present invention.

With reference to FIG. 6A, in the operation of the system of the invention, the first step is to prepare the structure, as indicated in block (100). This basically involves removing all heat-sensitive items from the enclosure or, in some cases, covering heat sensitive items, such as electronic devices and plastic items, with thermal insulation material. All material that has a flash/melt point at or below the maximum temperature to be used (such as candles, lipstick, etc.) must be removed.

Typically, the preparation of the structure also includes physical cleaning of contaminated areas of the structure (102), which may be preformed while the area is under a negative pressure. This can include vacuuming, wiping, scraping, etc. of various surfaces which have been contaminated with harmful biological contaminants, such as mold, fungi or bird, rodent or insect debris, etc. In extreme cases, this may require the removal of carpeting, section of walls, etc. However, the invention is intended to neutralize and remove these biological and organic contaminants without requiring resort to such extreme measures in some instances.

In one embodiment, particularly when treating the structure 12 for mold and fungi, borates, and preferably boric acid, are dispersed within the structure 12 at locations, preferably, where mold and fungi are likely to be encountered. Boric acid, $H_3BO_3$, is a white crystalline, oxygen-bearing acid of boron found in certain minerals and volcanic waters or hot springs in certain mineral deposits. Boric acid, or salts of boric acid, borates, traces of boron are necessary for growth of land plants and thus are indirectly essential for human life. In excessive quantities, however, borates may act as unselective herbicides. The most common source of boric acid is borate, sodium tetraborate or borax, which occurs naturally in salt beds. Boric acid may be obtained by treating borate with sulfuric acid. Boric acid is commonly used as a mild antiseptic for burns and surface wounds and comprises a major ingredient in eye lotions. Among its other important applications is its use as a fire retardant in fabrics. Importantly, boric acid is non-toxic to humans and animals and is ecologically benign in low concentrations.

Applying boric acid using conventional applicator methods and devices, i.e., dusting boric acid as a conventional insecticide as dust, spraying a solution or slurry or dispersion of boric acid, etc., coupled with heating the air within the enclosure, advantageously improves mold, fungi and pest (termite) abatement within the structure 12. The borates may be used in pre-treating contents of an enclosure, such as building materials, lumber, etc. or in post-treating such contents after application of heat.

A plurality of temperature indicating and pressure measuring probes 14 and 18 are placed in predetermined locations as indicated in block (104) to assure that the required temperature levels are achieved. In some cases the probes 14 can be read directly, although preferably they are connected by wires or wireless means to the console 16, so that all probes 14 and 18 can be monitored conveniently and the data recorded in real time.

When the enclosed structure 12 is sealed, at least one inlet duct 24 and at least one outlet duct 26 are then installed as indicated in block (106). Generally, a plurality of inlet ducts 24 is preferred. Although each duct 24 may enter the enclosed structure 12 separately, the use of one inlet duct 24 connected to a manifold from which plural ducts extend to predetermined locations within the enclosed structure 12 is preferred. Ducts 24 may enter the structure 12 through any suitable opening, such as an open window or door with the remainder of the window or door blocked by a panel. In some instances, such as when treating vehicles, tenting may actually be required or desired to treat the structure 12. However, in most instances such tenting is not required.

The appropriate air scrubbing filters 30 and vacuum devices 28 for facilitating the removal of the heated air and filtering the harmful substances therefrom, is installed, as indicated in block (108).

When the components of the system 10 have been properly prepared and positioned, heated air is directed into the inlet ducts (110). The desired pressure is established within the structure 12 (112) and the manometer or other pressure sensing device is used to verify that a sufficient pressure is present (114). In some instances, a positive pressure is actually desired wherein the ingress of heated air flow into the containment area exceeds the egress air flow from the negative air machines 28. Such positive pressure may be desired to force the contaminants to aerosolize or otherwise enter the circulated air. Typically, a negative air pressure within the structure 12 is desirable, by removing air more quickly than it is introduced, to ensure the removable of the contaminants therefrom and to promote circulation of the air. In any event, a negative pressure will be applied to the structure 12 at some point of the process in order to remove the aerosolized contaminants and filter them. This is accomplished using the vacuum/blower device 28 and filter 30 as described above. Using the pressure measuring manometer device 18, the internal pressure of the structure is measured and it is verified that sufficient negative pressure is present (114). Often the establishment of negative pressure is performed before any heat is introduced into the structure in order to begin the removal of any loose and aerosolized contaminants, and prevent their sporulation before heat is introduced.

The heated air is then re-circulated into the inlet ducts (118). Flow of the heated air through the enclosed structure 12 may range in time from a few hours to several days to provide optimum results. During this time, the temperature probes 14 are monitored (120) and these results recorded in real time (122) to ensure that the intended areas within the structure 12 are properly treated.

The heated air which has been circulated through the structure 12 is continually removed through an air scrubber filter to remove the remains of the destroyed organisms and VOCs. Biocides, such as ozone, or even moisture may be added to the heated air to enhance the treatment effect.

At any time during system operation, the inlet and outlet ducts 24 and 26 may be moved to assure uniform temperatures throughout the structure, as indicated by the temperature probes 14 and temperature monitoring console 16.

Figure 6B:
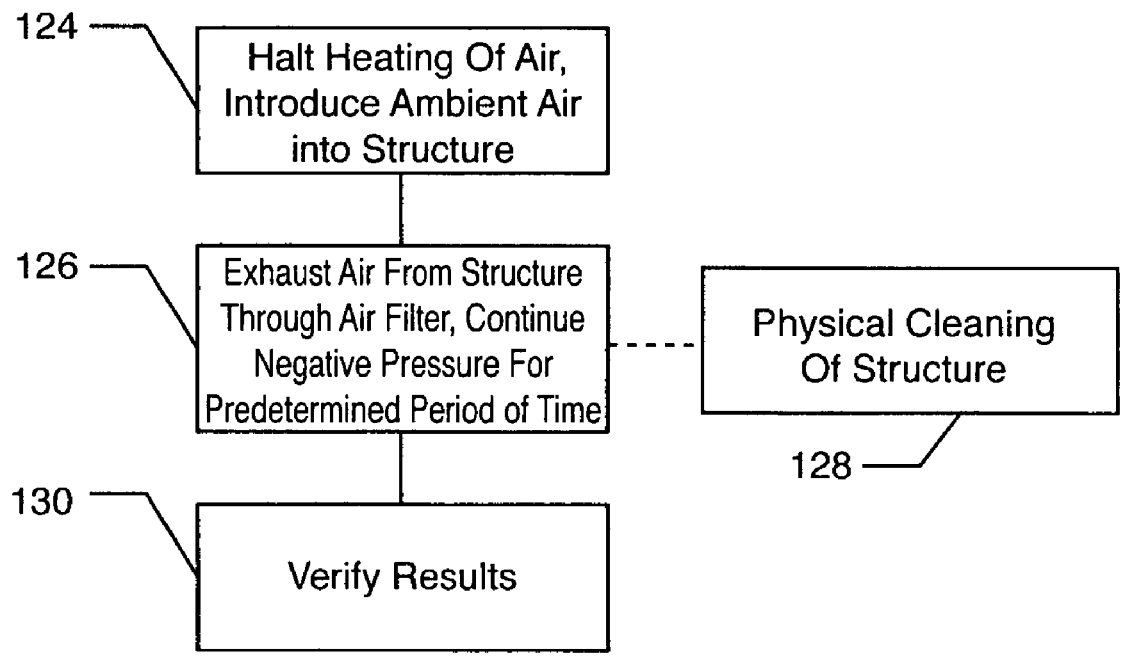

With reference now to FIG. 6B, after a predetermined period of time in which it has been determined that the harmful biological organisms and agents have been destroyed, moisture, if previously introduced is removed from the heated airstream, and after sufficient drying has taken place, the heating of air is halted and non-heated ambient air is introduced into the structure (124). The airfrom the structure is then exhausted through the air filter while the negative pressure is maintained for a predetermined period of time (126). These steps are taken in order to prevent any viable fungi, molds, etc. from sporulating or the like as such organisms when threatened with destruction will often sporulate or form cysts or the like to facilitate the survival of the organisms and their progeny. The aggressive air flow through the structure continues to remove the harmful organisms, organic substances, etc., for some time.

This entire process may often be completed in five to twelve hours, for example, allowing a business to be closed for only one day or a residential structure to be fully treated during a typical work or school day. However, in certain circumstances, such as in the case of large structures or high levels of harmful substances within the structure, the process may be extended to several days or more to ensure that the structure is properly treated. It has been found that while harmful organisms are killed and removed during this process, the reduction of the VOCs actually continues for some time after treatment. Placing a filtering system within the structure and/or opening a window to allow the structure 12 to properly vent is believed to be adequate to remove these residual compounds.

In certain instances, the structure 12 is then physically cleaned (128) after the aforementioned steps have been performed. For example, when dealing with the hanta virus, the health concerns of the workers dictate that the virus be killed and removed to the greatest extent possible. Then, after the virus has been destroyed and removed to the greatest extent possible utilizing the aforementioned steps, workers can enter the structure and physically remove rodent droppings and the like which may contain the neutralized viruses. Samples and specimens may be taken of the previously contaminated areas to verify the desired results (130) and a physical examination of the structure can be used to verify the removal of the contagions and harmful substances.

Although several embodiments have been described in detail for purposes of illustration, various modifications may be made without departing from scope and spirit of the invention. Accordingly, the invention is not to be limited, except as by appended claims.

What is claimed is:

1. A process for treating a passenger occupiable vehicle or building structure at least partially contaminated with harmful microorganisms or insects or having objects therein contaminated with microorganisms or insects, comprising the steps of:

substantially enclosing at least a portion of the structure to be treated;

heating ambient air within the structure to a temperature of between 110° F. to 400° F. to cause the harmful microorganisms or insects in the structure to be destroyed or migrate into the ambient air;

monitoring the temperature in the structure until the temperature is achieved;

passing the heated air from the structure through a filter;

recirculating the filtered and heated air into the structure; and directing non-heated ambient air into the structure after a predetermined time of directing heated air into the structure, while continuing to remove the air through the filter.

2. The process of claim 1, including the step of physically cleaning a contaminated portion of the structure.

3. The process of claim 1, including the step of physically cleaning a contaminated portion within the structure after determining that adequate treatment has occurred.

4. The process of claim 1, including the step of distributing heated air into the structure.

5. The process of claim 4, including the step of introducing moisture into the heated air.

6. The process of claim 1, wherein the filter comprises a high or ultra-high efficiency particulate arrestance filter.

7. The process of claim 1, wherein the filter comprises a carbon filter.

8. The process of claim 1, including the step of protecting heat-sensitive articles within the structure.

9. The process of claim 8, including the step of covering the articles with an insulated mat.

10. The process of claim 1, including the step of establishing a pressure within the structure and monitoring the pressure within the structure.

11. The process of claim 10, including the step of positioning a manometer within the structure to measure the pressure within the structure.

12. The process of claim 10, including the step of creating a negative pressure within the structure and monitoring pressure levels within the structure to verify adequate negative pressure.

13. The process of claim 1, including the step of aggressively moving air within the structure to aerosolize biological and organic substances to facilitate their removal.

14. The process of claim 1, including the step of positioning a plurality of temperature probes at predetermined locations relative to the structure.

15. The process of claim 1, wherein the structure comprises at least a portion of a building.

16. The process of claim 1, including the step of irradiating contents within the structure with ultra-violet light.

17. The process of claim 1, including the step of irradiating the heated air with ultra-violet light.

18. The process of claim 1, including the step of introducing moisture or a biocide into the heated air.

19. The process of claim 1, wherein the structure is selected from the group consisting of at least a portion of a building or a vehicle.

20. A process for treating a passenger occupiable vehicle or building structure contaminated with microorganisms or insects or having objects therein contaminated with microorganisms or insects, comprising the steps of:

substantially enclosing at least a portion of the structure to be treated;

introducing heated air of a temperature of between 110° F. to 400° F. into the structure to cause the microorganisms in the structure to be destroyed and/or migrate into the ambient air;

monitoring the temperature in the structure until the temperature is achieved;

aggressively moving air within the structure to aerosolize at least a portion of the microorganisms to facilitate their removal;

passing the heated air carrying the microorganisms through a high or ultra-high efficiency particulate arrestance filter;

recirculating the filtered and heated air within the structure; and directing non-heated ambient air into the structure after a predetermined time of directing heated air into the structure, while continuing to remove the air through the filter.

21. The process of claim 20, including the step of introducing moisture or a biocide into the heated air.

22. The process of claim 20, wherein the enclosed structure comprises at least a portion of a building or a vehicle.

23. The process of claim 20, including the step of physically cleaning a contaminated portion of the structure.

24. The process of claim 20, including the step of distributing heated air into the structure.

25. The process of claim 20, including the step of protecting heat-sensitive articles within the structure.

26. The process of claim 20, including the step of establishing a pressure within the structure and monitoring the pressure within the structure.

27. The process of claim 20, including the step of positioning a plurality of temperature probes at predetermined locations relative to the structure.

28. The process of claim 20, including the step of irradiating heated air or contents within the structure with ultra-violet light.

29. The process of claim 20, including the step of positioning a plurality of temperature probes at predetermined locations within the structure.

30. The process of claim 20, including the step of positioning a pressure measuring device within the structure to measure the pressure within the structure.

\* \* \* \* \*